United States Patent
Otsubo et al.

(10) Patent No.: US 7,329,244 B2
(45) Date of Patent: Feb. 12, 2008

(54) PULL-ON DISPOSABLE DIAPER

(75) Inventors: Toshifumi Otsubo, Kagawa-ken (JP); Nariaki Shimoe, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 142 days.

(21) Appl. No.: 11/056,277

(22) Filed: Feb. 14, 2005

(65) Prior Publication Data

US 2005/0143711 A1 Jun. 30, 2005

Related U.S. Application Data

(63) Continuation of application No. PCT/JP2003/010668, filed on Aug. 22, 2003.

(30) Foreign Application Priority Data

Aug. 31, 2002 (JP) ............................. 2002-294231
Sep. 26, 2002 (JP) ............................. 2002-281774

(51) Int. Cl.
A61F 13/15 (2006.01)
(52) U.S. Cl. .................. 604/385.201; 604/385.01; 604/385.21; 604/385.24; 604/385.25; 604/385.26
(58) Field of Classification Search ......... 604/385.201, 604/385.01, 385.21, 385.24, 385.25, 385.26
See application file for complete search history.

(56) References Cited

U.S. PATENT DOCUMENTS

| | | | | |
|---|---|---|---|---|
| 3,710,797 A | * | 1/1973 | Marsan | 604/385.201 |
| 3,724,646 A | * | 4/1973 | Enloe | 604/365 |
| 3,744,494 A | * | 7/1973 | Marsan | 604/378 |
| 3,774,610 A | * | 11/1973 | Eckert et al. | 604/365 |
| 3,848,595 A | * | 11/1974 | Endres | 604/385.201 |
| 3,924,627 A | * | 12/1975 | Nystrand | 604/365 |
| 3,968,799 A | * | 7/1976 | Schrading | 604/365 |
| 6,165,160 A | * | 12/2000 | Suzuki et al. | 604/385.201 |
| 2002/0068919 A1 | * | 6/2002 | Shinohara et al. | 604/385.27 |

FOREIGN PATENT DOCUMENTS

| | | |
|---|---|---|
| EP | 1 177 782 A1 | 2/2002 |
| JP | 47-36734 U | 12/1972 |
| JP | 48-20638 U | 3/1973 |
| JP | 50-21845 | 3/1975 |
| JP | 50-33044 | 3/1975 |
| JP | 63-32516 U | 3/1988 |
| JP | 2003-010244 | 1/2003 |

* cited by examiner

*Primary Examiner*—Jacqueline F. Stephens
(74) *Attorney, Agent, or Firm*—Lowe Hauptman & Berner LLP

(57) ABSTRACT

A pull-on disposable diaper has a body fluid absorbing component folded inward in a transverse direction of the diaper so that a width of the body fluid absorbing component may be reduced in a crotch covering region. In vicinities of leg-holes, elastic members intersect transversely opposite side edges of the body fluid absorbing component above points X, Y at which the side edges of the body fluid absorbing component intersect folding guides.

1 Claim, 12 Drawing Sheets

PULL-ON DISPOSABLE DIAPER

This application is a continuation of International Application No. PCT/JP2003/010668 filed Aug. 22, 2003, which claims priority to Japanese Application Ser. Nos. 2002-294231 filed on Aug. 31, 2002 and 2002-281774 filed Sep. 26, 2002, all of which are hereby incorporated by reference herein in their entirety.

BACKGROUND OF THE INVENTION

This invention relates to a pull-on disposable diaper.

Figure 12:
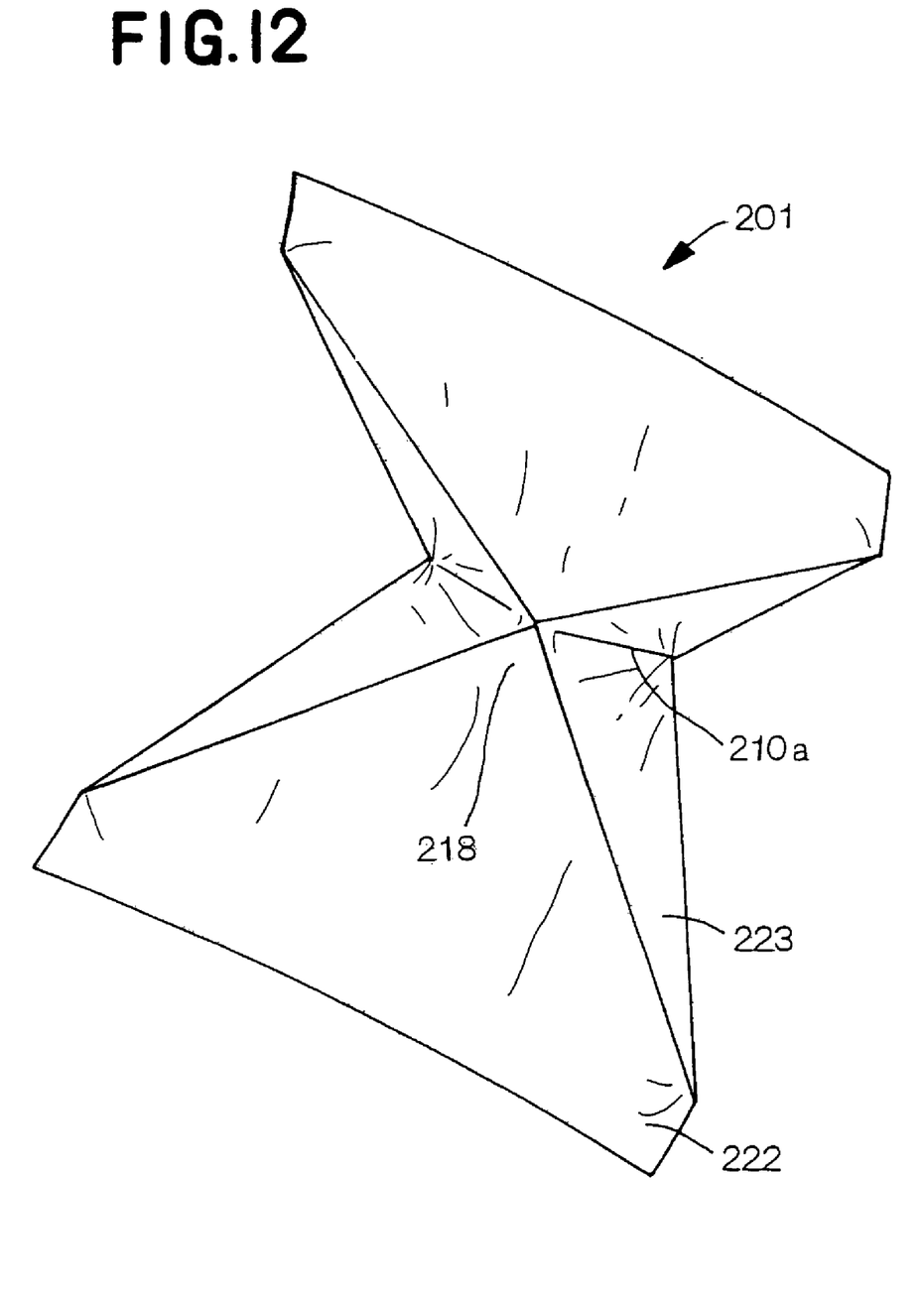
FIG. 12 is a perspective view showing a conditional diaper.

A foldup-type disposable diaper 201 shown in FIG. 12 of the accompanying drawings is disclosed in Japanese Patent Application Publication No. 1975-33044A. This diaper 201 is composed of a liquid-absorbent pad, a liquid-pervious inner sheet 222 and a liquid-impervious outer sheet 223 so as to present a rectangle and this rectangle is then folded along a transversal 210a orthogonal to long sides of the rectangle in two halves in a longitudinal direction. Simultaneously, the rectangle is tucked from its transversely opposite edges inwardly of the diaper, more specifically, toward a middle point of the transversal 210a so as to form pockets 218. Surface sections of the sheet 223 facing each other as the rectangle is tucked inward in this manner are partially joined to each other in order to prevent the respective pockets 218 from getting out of initial shapes thereof even after the diaper has been developed to be put on the wearer's body. The diaper arranged in the manner is effective to avoid leakage of body fluids regardless of its rectangular shape because a region of the diaper destined to cover the wearer's crotch region is sufficiently narrow to be placed closely against the wearer's crotch region.

The diaper disclosed in the above-cited Publication intends to prevent the diaper from getting out of its initial shape by partially joining together the surface sections opposed to each other as the diaper is tucked. For the well known diaper with its body fluid absorbing component folded so that the width thereof may be reduced in the crotch covering region, it is important to maintain the folded shape even during use of the diaper. It is an object of the present invention to provide a pull-on disposable diaper improved so that the folded shape of the body fluid absorbing component may be reliably maintained even in the disposable diaper having elastic members in vicinities of the leg-holes and thereby leakage of body fluids may be reliably prevented.

SUMMARY OF THE INVENTION

In accordance with this invention, there is provided a pull-on disposable diaper having a height direction, a transverse direction being orthogonal to the height direction and a back-and-forth direction, the diaper being substantially symmetric about a longitudinal center line extending in the height direction and bisecting a dimension of the diaper in the transverse direction, the diaper having an inner surface facing a wearer's body, an outer surface facing wearer's clothes, the diaper being composed of a front waist covering region destined to cover a wearer's front waist region, a rear waist covering region destined to cover a wearer's rear waist region and a crotch covering region destined to cover a wearer's crotch region so as to define a pants-like configuration having a waist-hole and a pair of leg-holes, and provided on the inner surface with a body fluid absorbing component extending over the crotch covering region and further extending into the front and rear waist covering regions.

The improvement according to the present invention further comprises the body fluid absorbing component comprising a liquid-absorbent core and a liquid-pervious cover sheet at least partially covering the core, having an inner surface facing the wearer's body, an outer surface facing away from the wearer's body and transversely opposite side edges extending parallel to each other beyond the crotch covering region into the front and rear waist covering regions and connecting the inner and outer surfaces to each other, the body fluid absorbing component being formed in the crotch covering region with a first folding guide extending from a transversely middle point between transversely opposite side edges to respective the side edges in the front waist covering region so as to describe a substantially V-shape, a second folding guide extending from a transversely middle point between transversely opposite side edges to respective the side edges to respective the side edges in the rear waist covering region so as to describe a substantially V-shape and a third folding guide extending in the transverse direction between the first and second folding guides, and the absorbing component being folded at least transversely opposite side edges on both sides of the longitudinal center line along the third folding guide so that the outer surfaces thereof face to each other and along the first and second folding guides so that the inner surfaces thereof face to each other; and elastic members provided in one of the front waist covering region, the rear waist covering region and the crotch covering region so as to intersect the side edges in vicinities of the leg-holes, one of the elastic members provided in the front waist covering region intersecting the side edges above first crossing points at which the side edges of the absorbing component intersect the first folding guide and one of the elastic members provided in the rear waist covering region intersecting the side edges above second crossing points at which the side edges of the absorbing component intersect the second folding guide.

The present invention includes the following embodiments. The elastic members lying in the vicinities of the leg-holes are leg-surrounding elastic members provided in a stretched state so as to extend downward from tops of the leg-holes along peripheral edges of the leg-holes, the leg-surrounding elastic members provided in the front waist covering region have lower end portions terminating above the first crossing points and the leg-surrounding elastic members provided in the rear waist covering region have lower end portions terminating above the second crossing points.

The elastic members lying in the vicinities of the leg-holes extend substantially horizontally position in the transverse direction of the diaper.

DETAILED DESCRIPTION OF THE PREFERRED EMBODIMENTS

Details of the pull-on disposable diaper according to this invention will be more fully understood from the description given hereunder with reference to the accompanying drawings.

Figure 1:
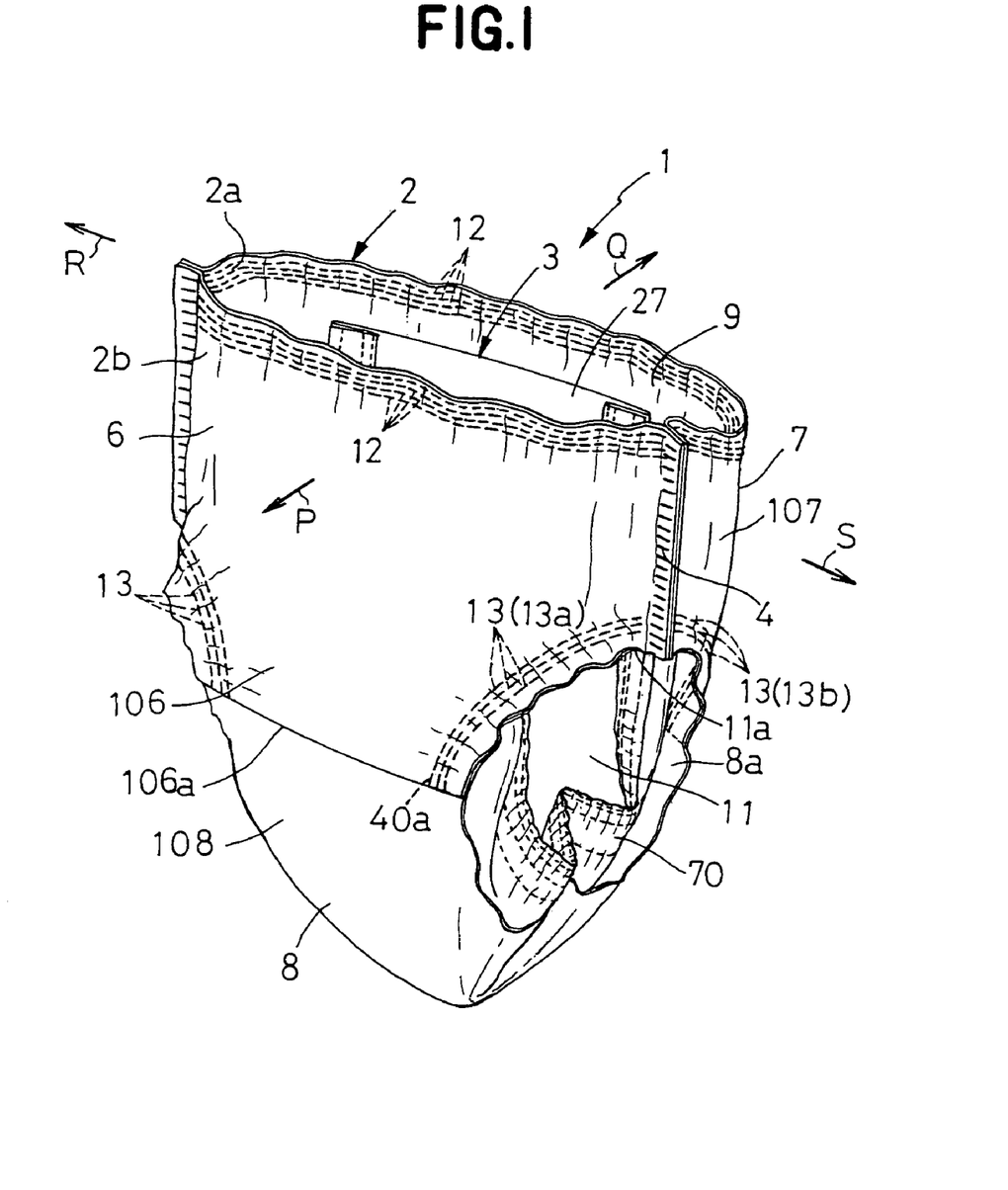
FIG. 1 is a perspective view showing a pull-on disposable diaper.
Figure 2:
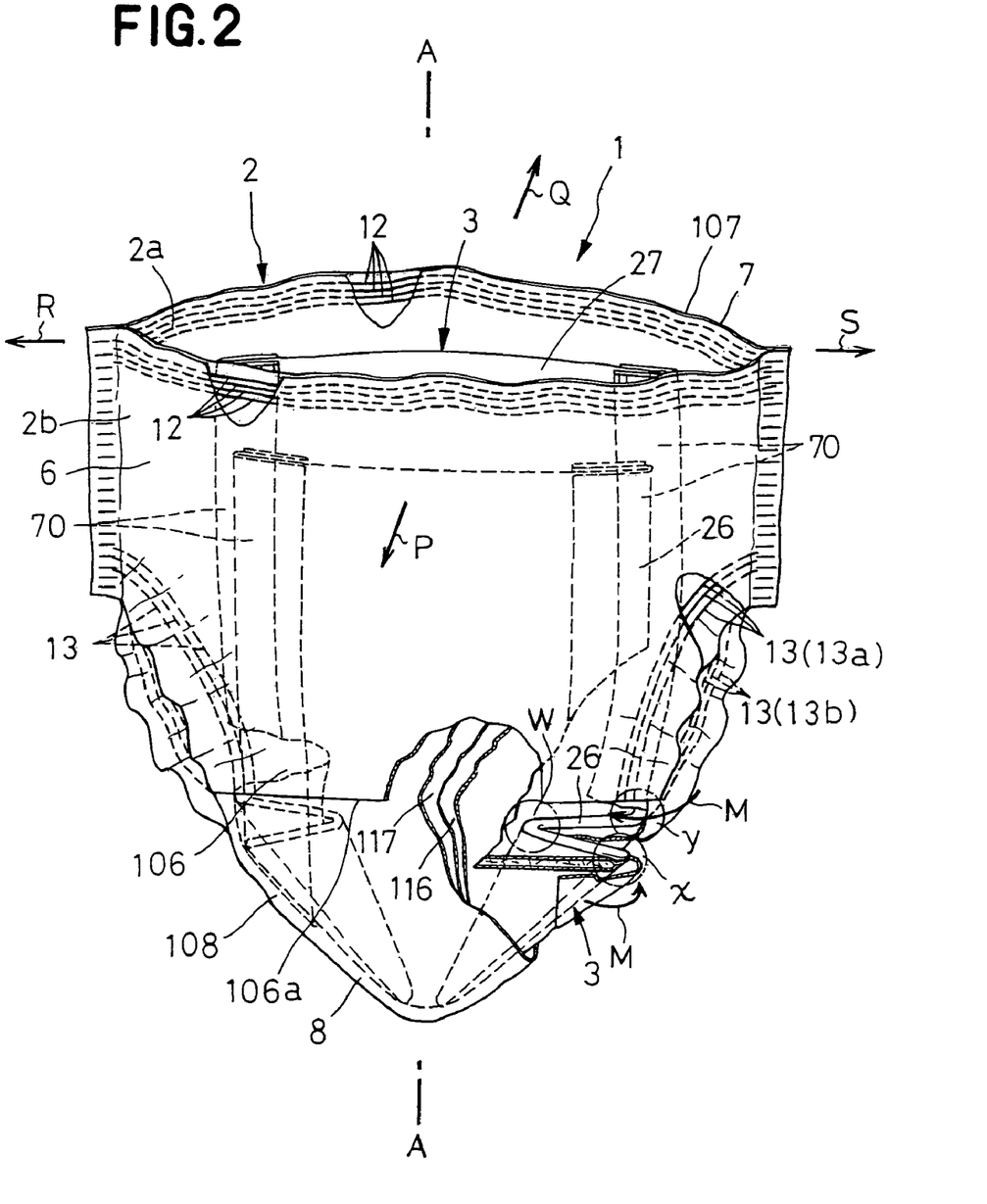
FIG. 2 is a partially cutaway perspective view showing the diaper of FIG. 1 as viewed from the front.

FIG. 1 is a perspective view showing a pull-on disposable diaper 1 and FIG. 2 is a partially cutaway perspective view showing this diaper 1 as viewed from the front. The diaper 1 has height and transverse directions orthogonal to each other and a back-and-forth direction. The height direction corresponds to a vertical direction in which a longitudinal center line A—A extends and bisects a width of the diaper 1 in FIG. 2, the back-and-forth direction corresponds to a direction indicated by arrows P and Q in FIG. 1 and direction corresponds to a direction indicated by arrows R, S in FIG. 1. The diaper 1 basically comprises a pants-like cover component 2 and a body fluid absorbing component 3 serving to contain body fluids absorbed.

The cover component 2 is formed by sheet material such as nonwoven fabric or plastic film and has an inner surface 2a facing diaper wearer's body and an outer surface 2b facing the wearer's clothes. This cover component 3 is composed of a front waist covering region 6, a rear waist covering region 7 and a crotch covering region 8 adapted to cover wearer's front, rear and crotch regions, respectively. In the crotch covering region 8, a front waist covering sheet 106 and a first crotch covering sheet 108 overlap each other (See FIG. 4) so that a lower end 106a of the front waist covering sheet 106 describes a straight line extending in the transverse direction. The front and rear waist covering regions 6, 7 are overlaid together along transversely opposite lateral edges of the diaper 1 and joined together along these opposite lateral edges by means of a plurality of spots 4 arranged intermittently in the height direction along the opposite lateral edges so that the front waist covering region 6, the rear waist covering region 7 and the crotch covering region 8 cooperate with one another to define a waist-hole 9 and a pair of leg-holes 11. The waist-hole 9 and the leg-holes 11 are provided along peripheral edges thereof with a plurality of elastic members 12, 13 attached thereto in a stretched state, respectively. The leg-surrounding elastic members 13 comprise front side leg-surrounding elastic members 13a extending downward from tops 11a of the respective leg-holes 11 toward a vicinity of the lower end 106a of the front waist covering sheet 106 on the front side of the diaper 1 and a rear side leg-surrounding elastic members 13b extending downward from the tops 11a of the respective leg-holes 11 toward a vicinity of a lower end 107a of a rear waist covering sheet 107. Apart of leak-barrier cuffs 70 can be seen inside one of the leg-hole 11.

Referring to FIG. 2, the crotch covering region 8 comprises a first crotch covering sheet 108 made of nonwoven fabric, a second crotch covering sheet 117 lying on the inner side of the first crotch covering sheet 108 and made of liquid-impervious film and an inner sheet 116 lying on the inner side of the second crotch covering sheet 117 and made of nonwoven fabric. The body fluid absorbing component 3 lies on the innermost side of these sheets 108, 117 and 116, i.e., on the inner surface 2a of the cover component 2.

The body fluid absorbing component 3 has transversely opposite side edges 26 extending over the crotch covering region 8 and further into the front and rear waist covering regions 6, 7 and longitudinally opposite end portions 27 extending in a waist-circumferential direction in the front and rear waist covering regions 6, 7, respectively. The transversely opposite side edges 26 are folded toward the longitudinal center line A—A bisecting a width of the diaper 1 so that the crotch covering region 8 may have its width reduced. Outside the respective side edges 26, leak-barrier cuffs 70 extend toward the longitudinally opposite end portions 27 of the absorbing component 3.

Figure 3:
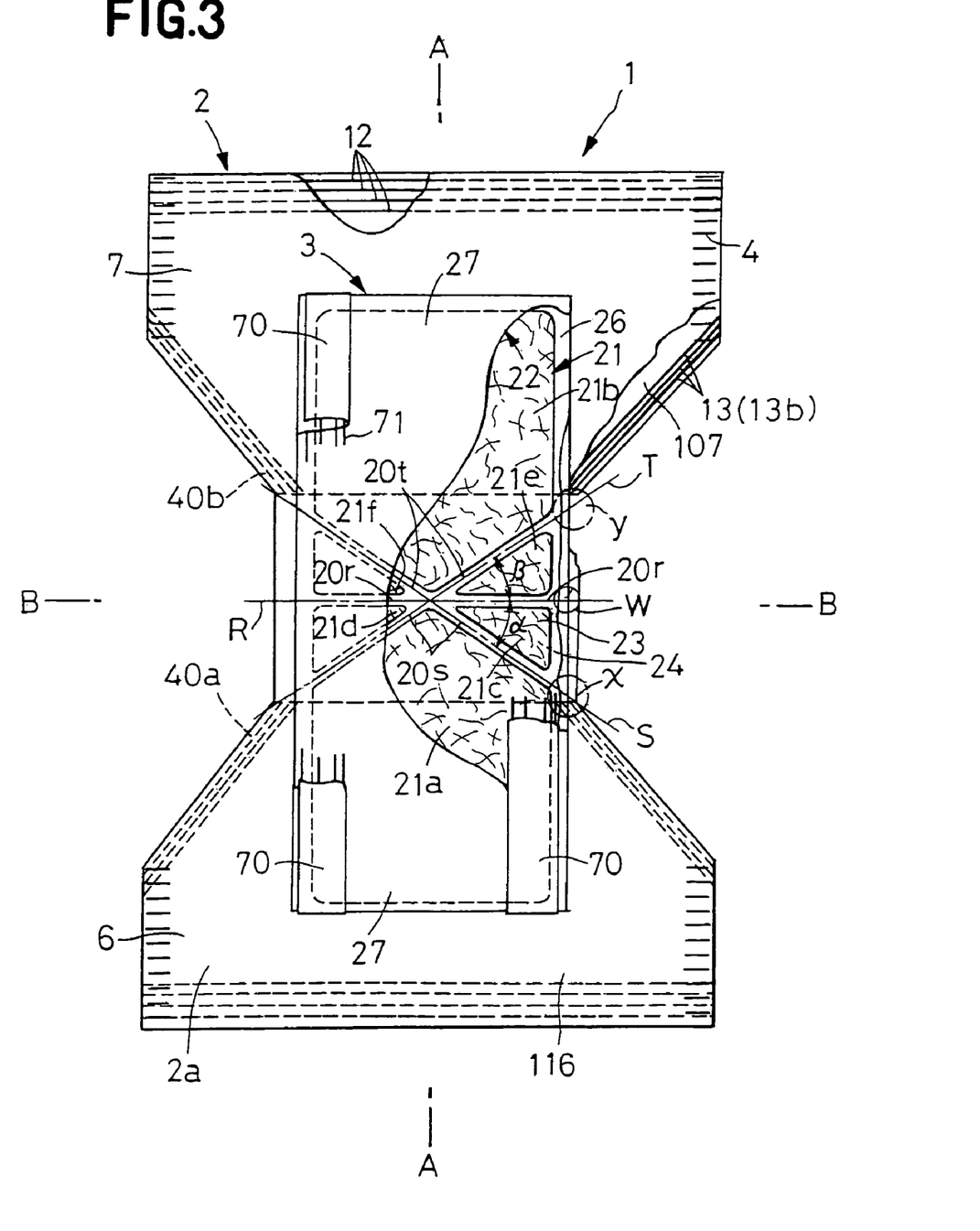
FIG. 3 is a developed view of the diaper of FIG. 1.
Figure 4:
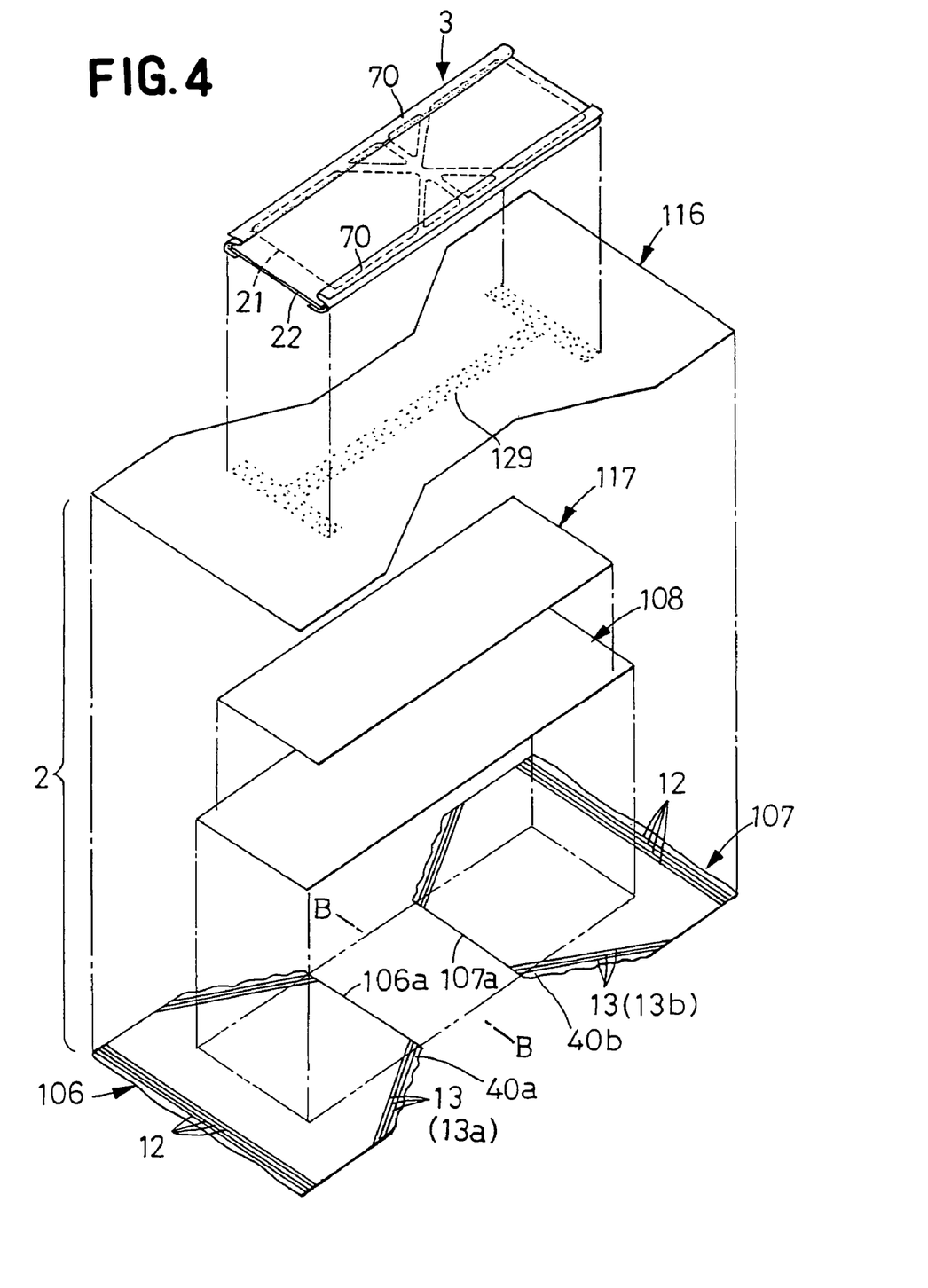
FIG. 4 is an exploded perspective view showing the diaper of FIG. 1.

FIG. 3 is a plan view showing the diaper 1 with the front and rear waist covering regions 6, 7 disconnected from each other along the arrays of the joining spots 4 and developed from the state shown in FIGS. 1 and 2 in the forth and back directions indicated by the arrows P and Q, respectively, and FIG. 4 is an exploded perspective view corresponding to FIG. 3. As shown in Figs., a transverse center line B—B extends in a direction which is orthogonal to the longitudinal center line A—A and bisects a length of the diaper 1. In the developed state as shown in FIG. 3, the diaper 1 is substantially symmetric about the longitudinal center line A—A and may be folded back along the transverse center line B—B to obtain the diaper 1 in the state as shown in FIG. 1.

Now the cover component 2 and the absorbing component 3 will be described in details with reference to FIGS. 3 and 4. The cover component 2 comprises the hexagonal front waist covering sheet 106 defining the front waist covering region 6 and a part of the crotch covering region 8, the hexagonal rear waist covering sheet 107 defining the rear waist covering region 7 and a part of the crotch covering region 8, and the first crotch covering sheet 108 defining a major part of the crotch covering region 8. The first crotch covering sheet 108 has its longitudinally opposite end portions joined to respective inner surfaces (upper surfaces as viewed in FIG. 4) of the front and rear waist covering sheets 106, 107 by means of a hot melt adhesive (not shown) so as to connected these sheets 106, 107 with each other. A second crotch covering sheet 117 made of rectangular liquid-impervious film lies on an inner surface of the first crotch covering sheet 108 and an hourglass-shaped inner sheet 116 lies on an inner surface of the second crotch covering sheet 117. The second crotch covering sheet 117 as shown in FIGS. is identical in shape as well as in size to the first crotch covering sheet 108 or slightly smaller than the first crotch covering sheet 108. The inner sheet 116 is substantially identical in shape as well as in size of an hourglass-shaped assembly comprising the front and rear waist covering sheets 106, 107 and the first crotch covering sheet 108. These sheets 106, 107, 108, 117, 116 are overlapped and intermittently joined to one another. The waist-surrounding elastic members 12 in a stretched state are interposed between the front waist covering sheet 106 and the inner sheet 116 and the leg-surrounding elastic members 13 in a stretched state are interposed between the rear waist covering sheet 107 and the inner sheet 116. A primary function required for the first crotch covering sheet 108 is to connect the front and rear waist covering sheets 106, 107 with each other and, so far as this function can be obtained, the first crotch covering sheet 108 may be smaller than the second crotch covering sheet 117.

The absorbing component 3 comprises a core 21 and a cover sheet 22 which is secured to the inner surface 2a of the cover component 2 by means of hot melt adhesive 129 in the middle of the transverse direction along the longitudinal center line A—A and the longitudinally opposite end portions 27. The absorbing component 3 is provided with the leak-barrier cuffs 70 at transversely opposite side edges 26. The cover sheet 22 is formed by liquid-pervious nonwoven fabric or perforated plastic film and the core 21 is formed by compressing water-absorbent material such as fluff pulp and super-absorbent polymer particles under an appropriate pressure and, if desired, wrapping this compressed water-absorbent material with a tissue paper or a nonwoven fabric made of thermoplastic synthetic fibers treated to be hydrophilic. The core 21 as shown in FIGS. presents a rectangular shape as a whole and has grooves 20r, 20s, 20t extending along a chain line R (third folding guide) extending in coincidence with the transverse center line B—B, a chain line S (first folding guide) extending from a central portion of the core 21 defined by an intersection of the longitudinal center line A—A and the transverse center line B—B to the transversely opposite side edges 26 in the front waist covering region 6 so as to describe a V-shape and a chain line T (second folding guide) extending so as to describe a V-shape from the central portion of the core 21 defined by the intersection of the longitudinal center line A—A and the transverse center line B—B to the transversely opposite side edges 26 in the rear waist covering region 7 so as to describe a V-shape. These grooves 20r, 20s, 20t divide the core 21 into core elements 21a, 21b, 21c, 21d, 21e, 21f. The groove 20r and the groove 20s intersect with each other at an angle α while the groove 20r and the groove 20t intersect with each other at an angle β. While the angles α and β are illustrated to be equal to each other, it is possible to set these two angles to be different from each other. In the crotch covering region 8, the absorbing component 3 is narrower than this crotch covering region 8, so lateral edges 8a of the crotch covering region 8 extend outward beyond the side edges 26 of the absorbing component 3 and form leg-circumferential flaps which define the respective leg-holes 11. The respective core elements 21a through 21f are intermittently secured to the cover sheet 22 or the tissue paper covering them by means of a hot melt adhesive so that a relative position of these core elements may be stabilized.

The sheets 106, 107, 108, 117, 116 and the absorbing component 3 placed upon one another and joined to one another as shown in FIGS. 3 and 4 are folded back along the transverse center line B—B with the absorbing component 3 inside and then the front and rear waist covering sheets 106, 107 and the inner sheet 116 are joined to one another at the joining spots 4 to obtain the pull-on disposable diaper 1. In this course, respective halves of the absorbing component 3 lying on both sides of the longitudinal center line A—A are folded toward this longitudinal center line A—A as shown in FIG. 2. Specifically, the absorbing component 3 is folded along the chain line R corresponding to the groove 20r so that the outer surface 24 (See FIG. 3) of the core element 21c is opposed to the outer surface 24 of the 21e while the outer surface 24 of the core element 21d is opposed to the outer surface 24 of the core element 21f. At the same time, the absorbing component 3 is folded along the substantially V-shaped folding guide formed by the chain line S in the front half of the absorbing component 3 so as to extend from the transversely middle point of the absorbing component 3 to the side edges 26 and along the substantially V-shaped folding guide formed by the chain line T in the rear half of the absorbing component 3 so as to extend from the transversely middle point of the absorbing component 3 to the side edges 26 so that the inner surface 23 of the core element 21a is opposed to the inner surfaces 23 of the respective core elements 21c, 21d while the inner surface 23 of the core element 21b is opposed to the inner surfaces 23 of the respective core elements 21e, 21f.

In the absorbent component 3 of the diaper 1 folded along the chain lines R, S, T serving as the folding guides, these chain lines R, S, T intersect each of the side edges 26 at points W, X, Y-at acute angles (See FIGS. 2 and 3). Portions of the side edge 26 defined between the crossing points W and X and between the crossing points W and Y extend inward in the transverse direction of the diaper 1. With this diaper 1 put on the wearer's body, the portion of the side edge 26 defined between the crossing points X and Y lies on an inner side of wearer's thighs and tends to move inwardly of the diaper 1 and to get nearer to the longitudinal center line A—A. As a result, the crossing points X and Y may sometimes move toward the inside of the leg-hole 11 in a direction indicated by an arrow M in FIG. 2. If the front and rear side leg-surrounding elastic members 13a, 13b extending from the tops point 11a of the leg-hole 11 have lower end portions 40a, 40b extending downward beyond the crossing points X, Y, there is a possibility that, in vicinities of the crossing points X, Y, the leg-surrounding elastic members 13 might extend from the outer side toward the inner side of the diaper 1 rather than in the leg-circumferential direction as portions of the absorbing component 3 in the vicinities of the crossing points X, Y move in the direction indicated by the arrow M. Such a condition would lead to an inconvenience, particularly in the rear side of the diaper 1 that the opposite lateral portions in the crotch covering region 8 might bite into a wearer's hip. In this case, it would be difficult for the portions of the absorbing component 3 in the vicinities of the crossing points X, Y to be reliably tightened around the wearer's legs and thereby to prevent body fluids from leaking sideways. The apprehension as has been described hereinabove is effectively eliminated by the present invention. Specifically, of the leg-surrounding elastic members 13 of the diaper 1, the lower end portions 40a of the front side leg-surrounding elastic members 13a extend in the direction in which the lower end portions 40a intersect the respective side edges 26 and terminate above the crossing points X, preferably 5 mm or more above the crossing points X. The lower end portions 40b of the rear side leg-surrounding elastic members 13b also extend in the direction in which the lower end portions 40b intersect the respective side edges 26 and terminate above the crossing points Y, preferably 5 mm or more above the crossing points Y. Such a unique arrangement is effective to avoid an anxiety that the lower end portions 40a, 40b of the front and rear side leg-surrounding elastic members 13a, 13b might move in the direction indicated by the arrow M and cause leakage of body fluids even if the portions of the absorbing component 3 in the vicinities of the crossing points X, Y move in the direction indicated by the arrow M. It should be understood that this diaper 1 is provided outside the respective side edges 26 of the absorbing component 3 with the leak-barrier cuffs 70 which are provided, in turn, with elastic members 71 (See FIG. 3) attached thereto in a stretched state in the longitudinal direction of the absorbing component 3. The leak-barrier cuffs 70 are adapted to rise above the inner side of the crotch covering region 8 and thereby to be closely placed around the wearer's legs from below as these elastic members 71 contract.

Figure 5:
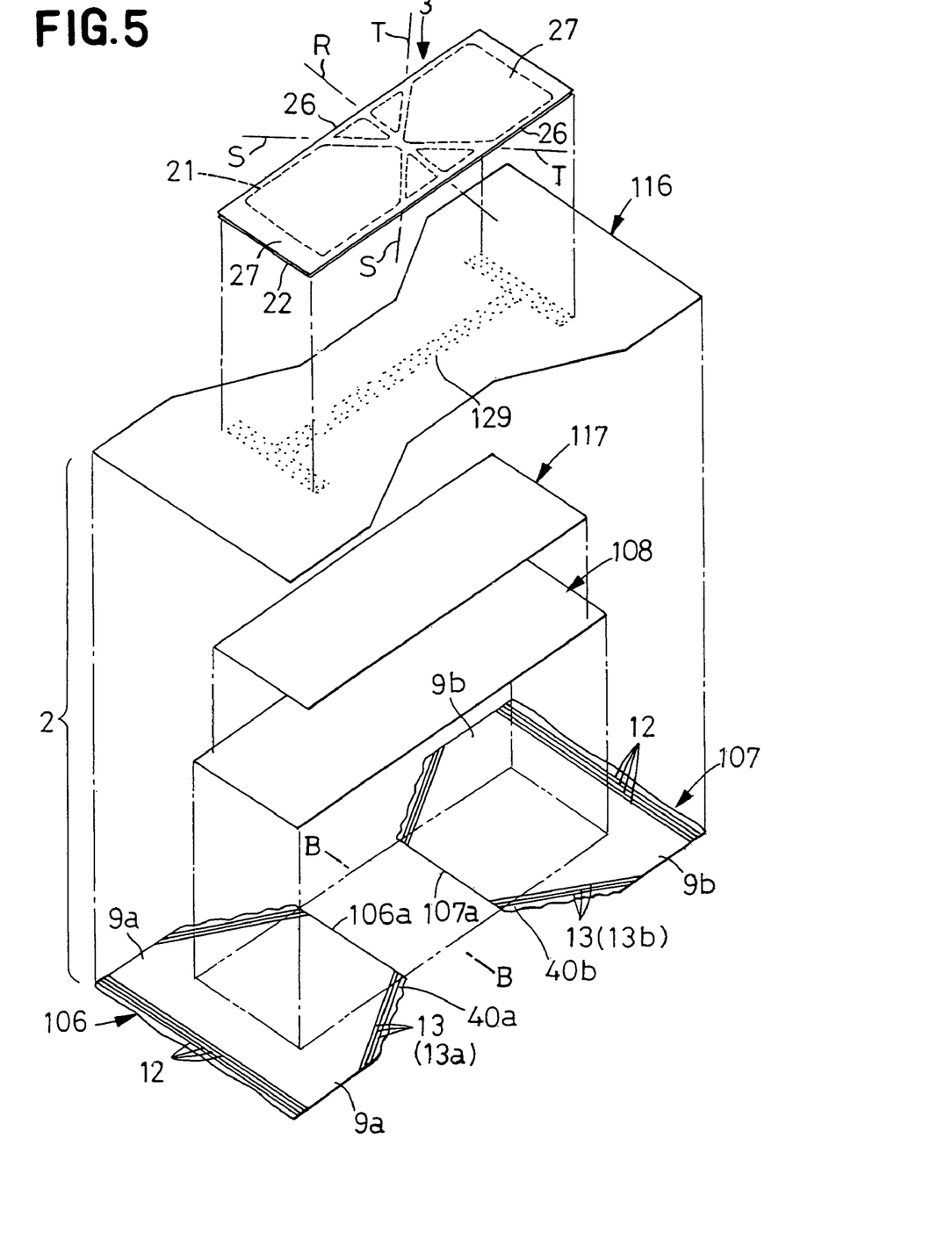
FIG. 5 is a view similar to FIG. 4 showing a preferred embodiment of the invention.
Figure 6:
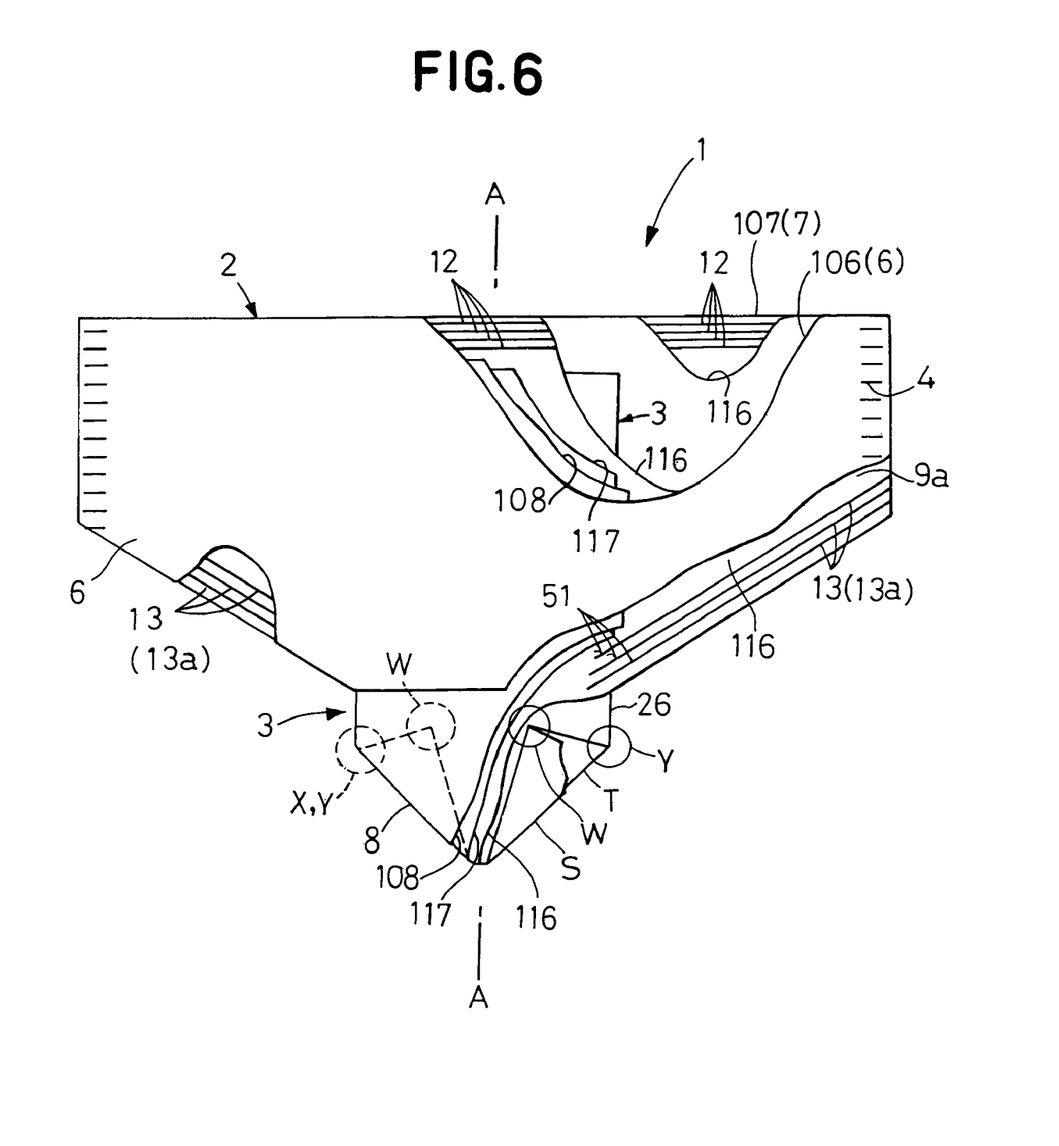
FIG. 6 is a partially cutaway plan view showing the diaper FIG. 5 after erected.

FIG. 5 is an exploded perspective view similar to FIG. 4 showing a preferred embodiment of the invention and FIG. 6 is a partially cutaway plan view showing the diaper 1 of FIG. 5 after erected. The diaper 1 of FIG. 5 is distinguished from the diaper of FIG. 4 in that the respective side edges 26 of the absorbing component 3 are not provided with the leak-barrier cuffs 70 shown in FIG. 4 and the front and rear covering sheets 106, 107 are identical to each other in size as well as in shape. Referring to FIG. 6, the elastic members 12, 13 are in a stretched state and the front waist covering sheet 106, the rear waist covering sheet 107, the first crotch covering sheet 108, the second crotch covering sheet 117 and the inner sheet 116 are placed upon one another and the absorbing component 3 has been folded in the crotch covering region 8 toward the longitudinal center line A—A. The core 21 wrapped with the cover sheet 22 is indicated by imaginary lines in FIG. 5 and only the portion of the absorbing component 3 which is invisible due to folding is indicated by imaginary lines in FIG. 6. Similarly to the case of the diaper 1 shown in FIG. 2, in the absorbent component 3 of the diaper 1 folded along the chain lines R, S, T serving as the folding guides as shown in FIG. 5, these chain lines R, S, T intersect each of the side edges 26 at points W, X, Y at acute angles. Referring to FIG. 6, the crossing points X, Y lie substantially in coincidence with each other so as to be placed upon each other. Of the leg-surrounding elastic members 13, the front side leg-surrounding elastic members 13a have respective lower end portions 51 obliquely extending downward from the side edges 9a of the front waist covering region 6 intersect the side edges 26 of the absorbent component 3 above the crossing points X, preferably at least 5 mm above the crossing points X. Though not shown, the rear side leg-surrounding elastic members 13a attached to the rear waist covering sheet 107 intersect the side edges 26 of the absorbent component 3 above the crossing points Y, preferably at least 5 mm above the crossing points Y. The diaper 1 according to this embodiment is, as is the case of FIG. 2, free from the anxiety that respective lower end portions 51 of the leg-surrounding elastic members 13 might move inwardly of the respective leg-holes 11 even when the crossing points W, X, Y of the absorbing component 3 move inwardly of the diaper 1 toward the center line A—A. In addition, there is no anxiety that the lower end portions 51 of the elastic members 13 might obstruct movement of the absorbing component 3 in the respective folded portions.

Figure 7:
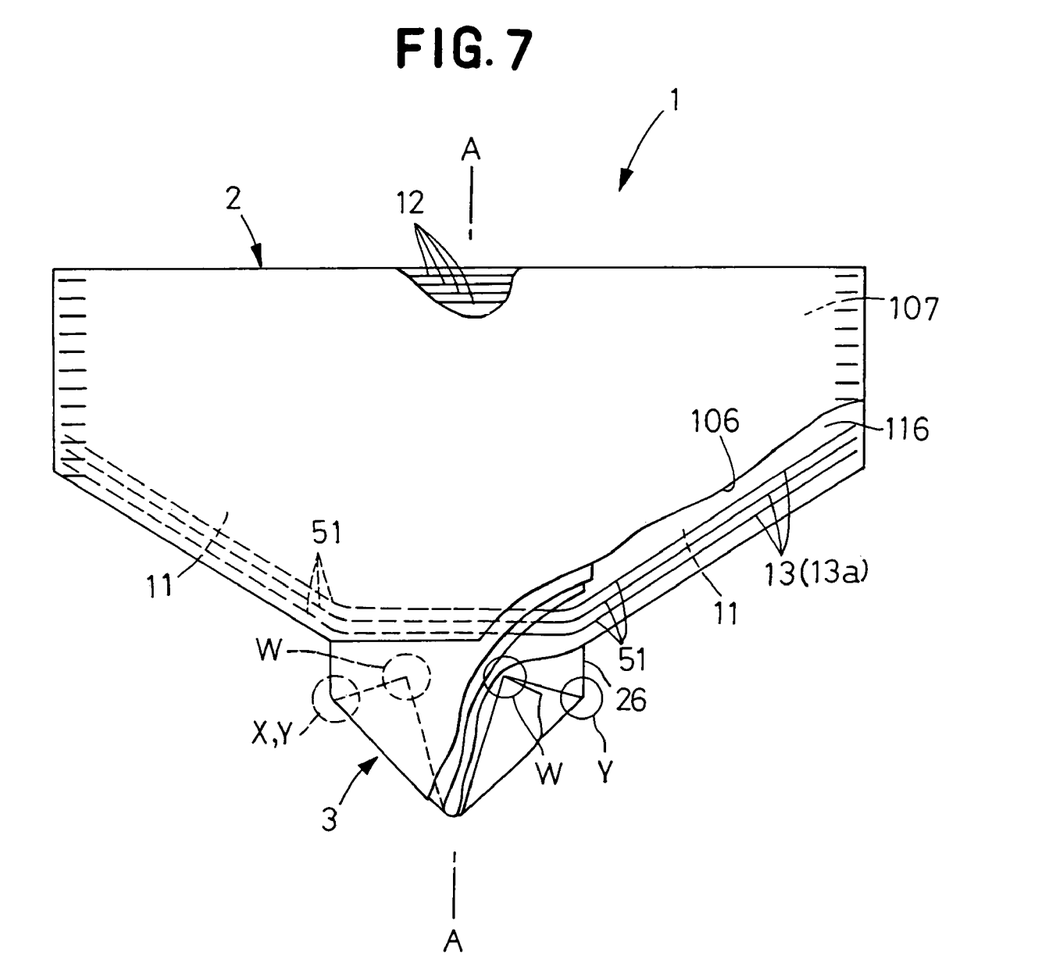
FIG. 7 is a partially cutaway plan view similar to FIG. 6 showing another embodiment of the invention.

FIG. 7 is a partially cutaway plan view similar to FIG. 6 showing another embodiment of the invention. The diaper 1 according to this embodiment is characterized in that the lower end portions 51 of the elastic members 13 attached to the front waist covering sheet 106 in a stretched state so as to extend along peripheral edges of the respective leg-holes 11 are connected to each other at the transversely middle point of the diaper 1. Though not shown, layout of the elastic members 13b attached to the rear waist covering sheet 107 is same as that of the elastic members 13a. The elastic members 13a intersect the side edges 26 of the absorbing component 3 above the crossing points X, Y appearing as the absorbing component 3 is folded, preferably at least 5 mm above the crossing points X, Y.

Figure 8:
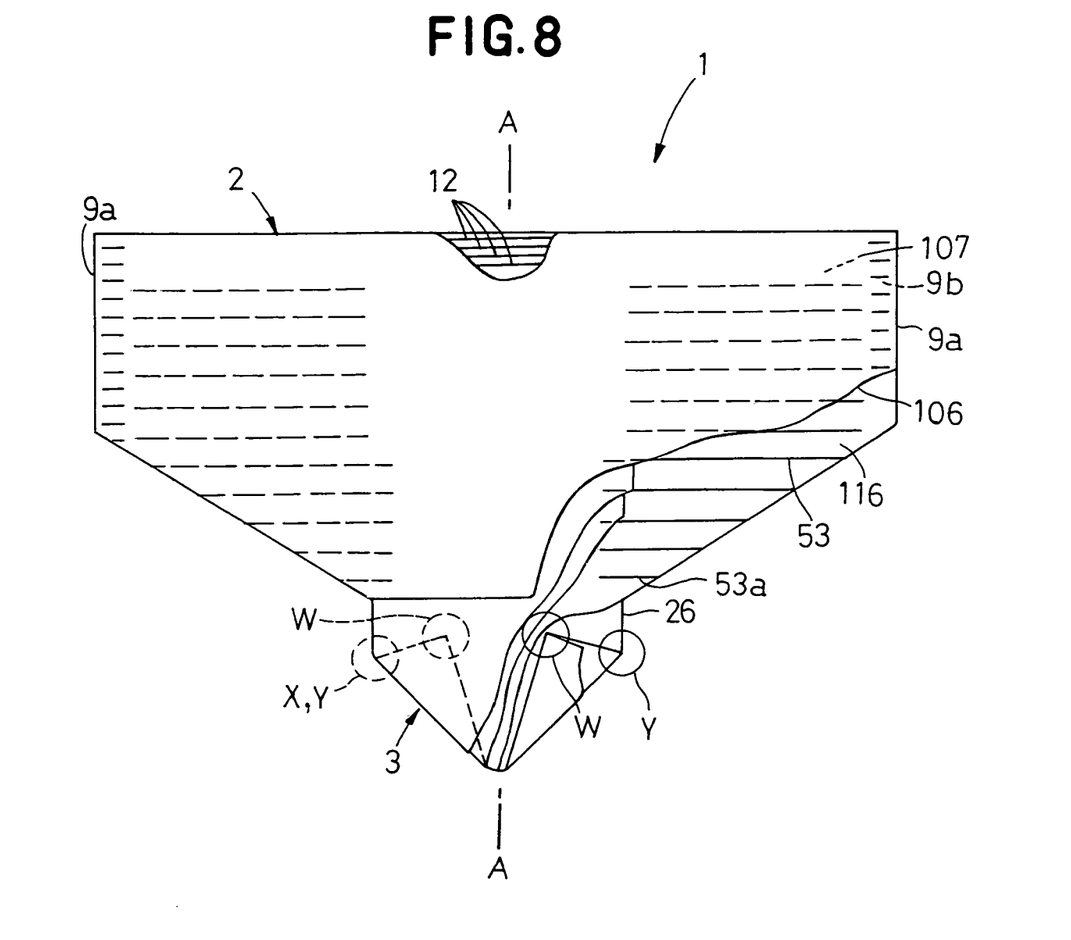
FIG. 8 is a partially cutaway plan view similar to FIG. 6 showing still another embodiment of the invention.

FIG. 8 is a partially cutaway plan view similar to FIG. 6 showing still another embodiment of the invention. The diaper 1 according to this embodiment is characterized in that the leg-surrounding elastic members 13 are replaced by a plurality of auxiliary elastic members 53 extending parallel to one another in waist-circumferential direction, i.e., horizontally as viewed in FIG. 8. These auxiliary elastic members 53 in a stretched state are interposed between the front waist covering sheet 106 and the inner sheet 116 as well as between the rear waist covering sheet 107 and the inner sheet 116 and secured to the front and rear waist covering sheets 106, 107 by means of a hot melt adhesive (not shown). Portions of the auxiliary elastic members 53 covered with the front waist covering sheet 106 are indicated by imaginary lines. These auxiliary elastic members 53 extend from the side edges 9a or 9b of the front waist covering sheet 106 or the rear waist covering sheet 107 (See FIG. 5), respectively, to vicinities of the side edges 26 of the absorbing component 3 so that these elastic members 53 may be arranged parallel to one another between immediately below the waist-surrounding elastic members 12 and the lower end portions of the front and rear waist covering sheets 106, 107 and the lowermost auxiliary elastic member 53a may intersect the side edges 26 above the crossing points X, preferably at least 5 mm above the crossing points X.

Figure 9:
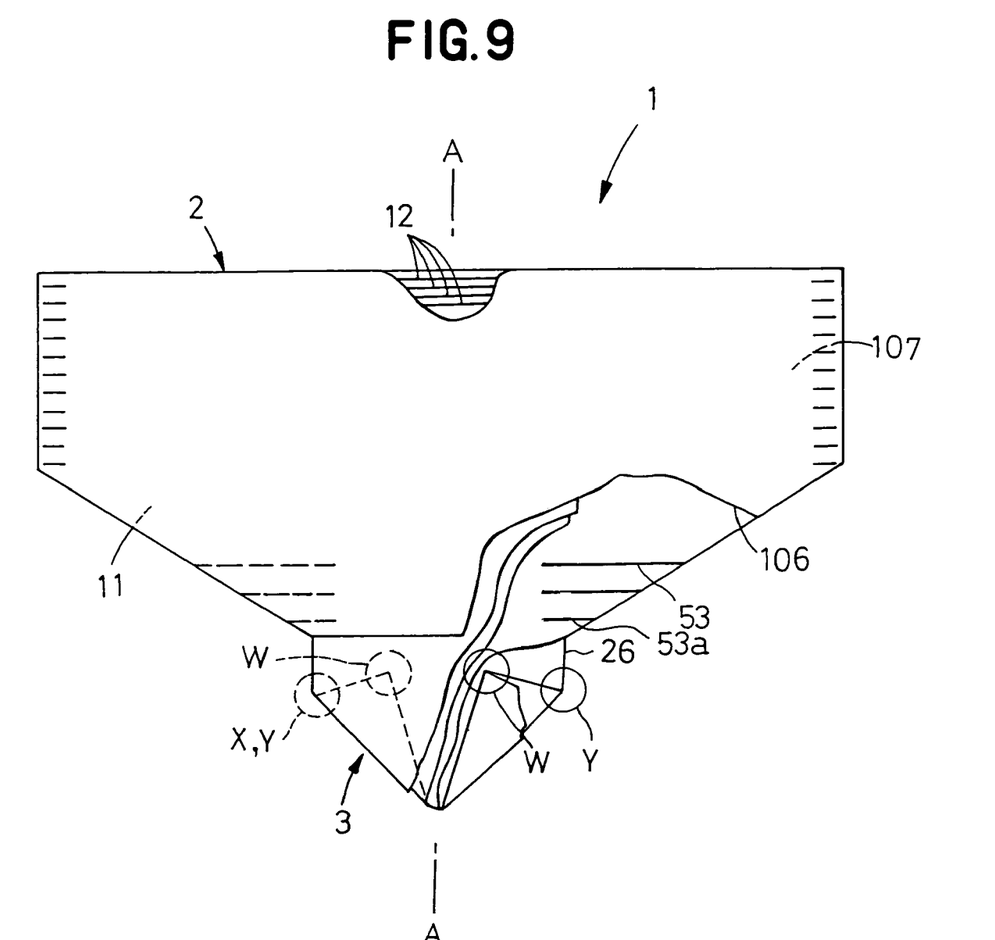
FIG. 9 is a partially cutaway plan view similar to FIG. 8 showing further another embodiment of the invention.

FIG. 9 is a partially cutaway plan view similar to FIG. 8 showing further another embodiment of the invention. The diaper 1 according to this embodiment is distinguished from the diaper 1 of FIG. 8 in that the auxiliary elastic members 53 are provided only in the lower end portions of the front and rear waist covering sheets 106, 107. Referring to FIG. 9, the lowermost auxiliary elastic member 53a intersects the side edges 26 above the crossing points X of the absorbing component 3, preferably at least 5 mm above the crossing points X.

Figure 10:
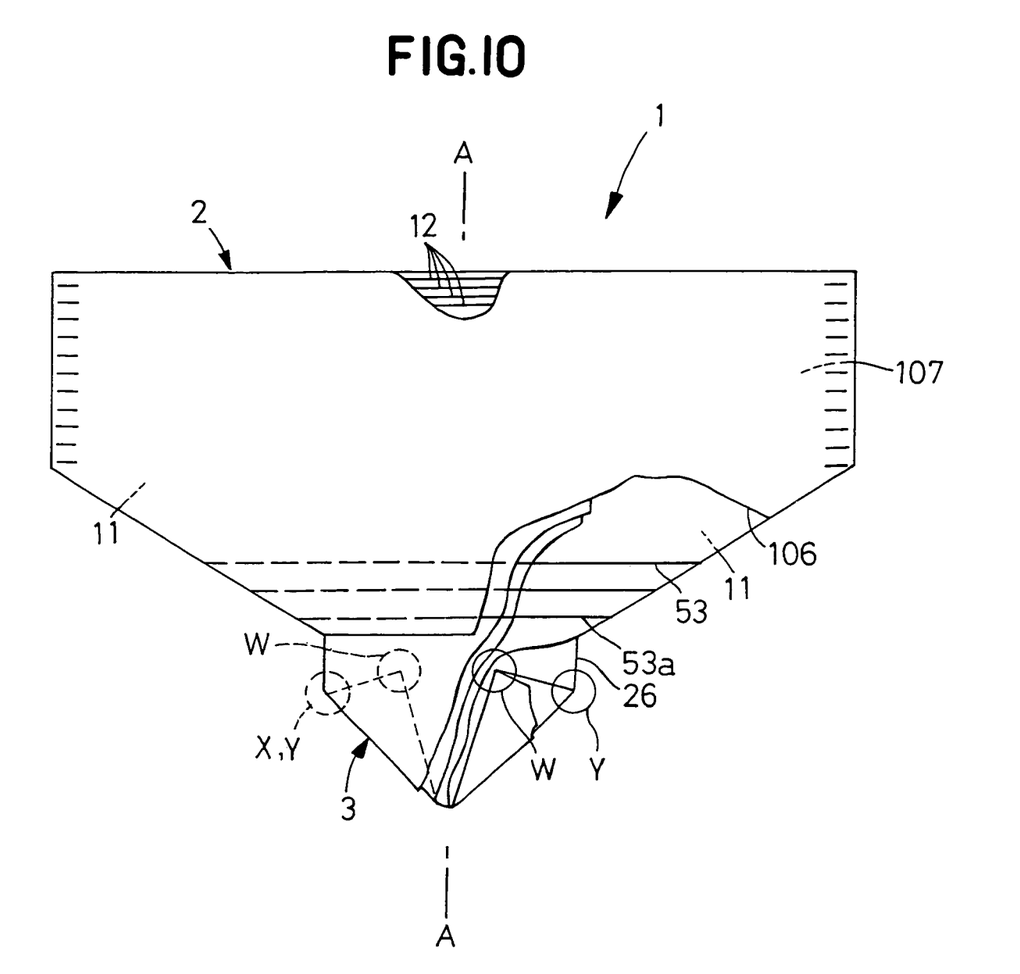
FIG. 10 is a partially cutaway plan view similar to FIG. 9 showing an additional embodiment of the invention.

FIG. 10 is a partially cutaway plan view similar to FIG. 9 showing an additional embodiment of the invention. The diaper 1 according to this embodiment is characterized in that the auxiliary elastic members 53 provided only in the lower end portions of the front and rear waist covering sheets 106, 107 extend across the absorbing component 3 to the peripheral portions of the leg-holes 11. These auxiliary elastic members 53 may be in a stretched state over the full length thereof or may be in non-stretched state only at the portions thereof extending across the absorbing component 3. Referring to FIG. 10, the lowermost auxiliary elastic member 53a intersects the side edges 26 above the crossing points X of the absorbing component 3, preferably at least 5 mm above the crossing points X.

Figure 11:
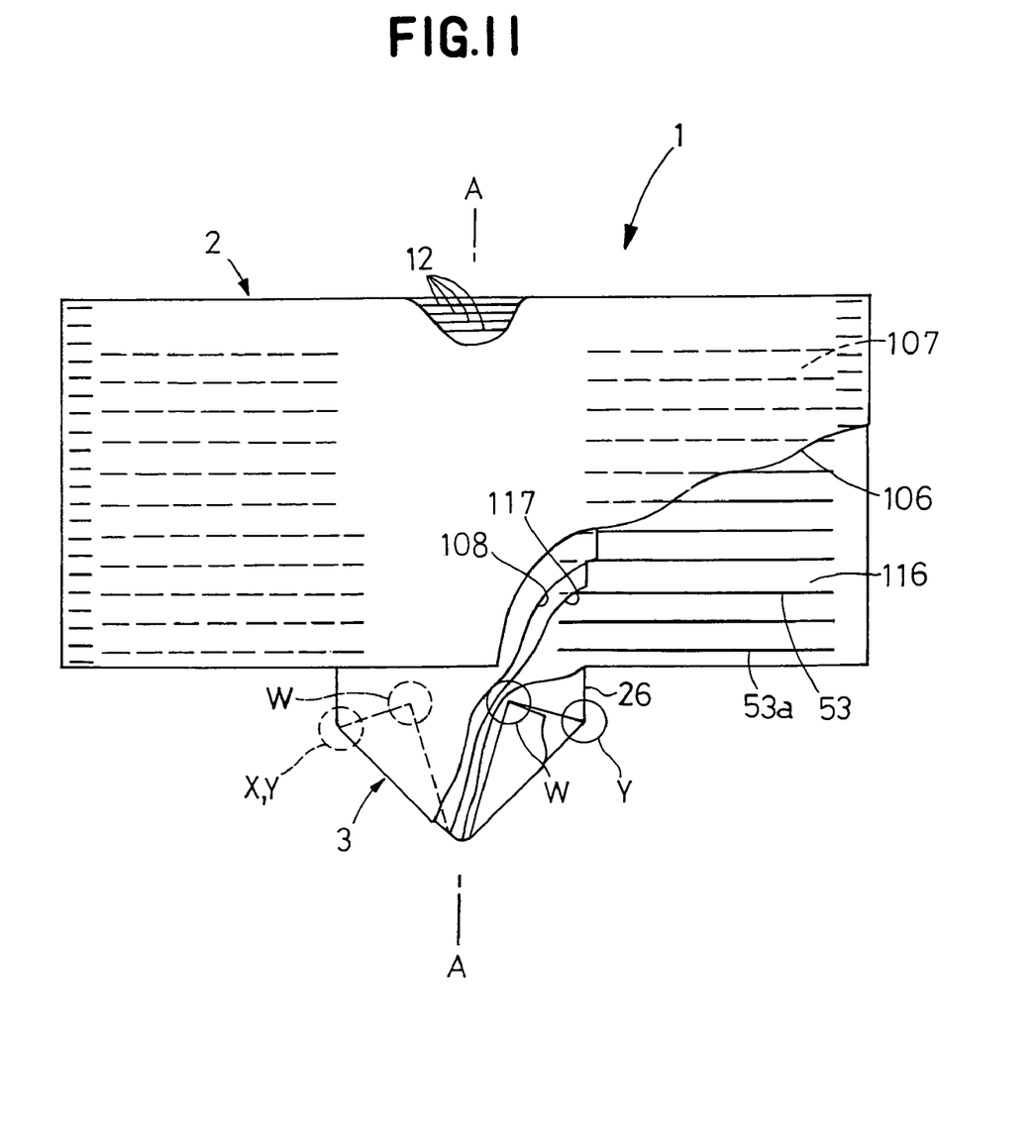
FIG. 11 is a partially cutaway plan view similar to FIG. 8 showing further additional embodiment of the invention.

FIG. 11 is a partially cutaway plan view similar to FIG. 8 showing further additional embodiment of the invention. The diaper 1 according to this embodiment is distinguished from the diaper 1 of FIG. 8 in that the front and rear waist covering sheets 106, 107 are not hexagonal but rectangular and the inner sheet 116 is substantially identical to these sheets 106, 107 in size as well as in shape. Layout of the auxiliary elastic members 53 is substantially same as the layout of those shown in FIG. 8 and the lowermost auxiliary elastic member 53a intersects the side edges 26 above the crossing points X of the absorbing component 3, preferably at least 5 mm above the crossing points X. The layout of the auxiliary elastic members 53 as shown in FIG. 11 may be replaced by the layout as shown in FIG. 9 or 10.

If these elastic members lie in the lateral side of the crossing points X, Y, these elastic members are preferably spaced apart from the crossing points X, Y at least by 5 mm while the invention has been described on the basis of the embodiments in which the leg-surrounding elastic members 13 as well as the auxiliary elastic members 53 intersect the side edges 26 above the crossing points X, Y of the absorbent component 3. It is also possible that the layouts of the leg-surrounding elastic members 13 and the auxiliary elastic members 53 on the front waist covering sheet 106 are different from those on the rear waist covering sheet 107. For example, the front waist covering sheet 106 may be adopted for the layout as shown in FIG. 6 and the rear waist covering sheet 107 may be adopted for the layout as shown in any one of the other figures.

The pull-on disposable diaper according to the present invention includes the body fluid absorbing component extending over the crotch covering region into the front and rear waist covering regions, in which the side edges of the absorbing component are folded inward in the transverse direction of the diaper so that the width of the absorbing component may be reduced in the crotch covering region. The elastic members lying in the vicinities of the leg-holes intersect the side edges of the absorbing component above the crossing points appearing as the absorbing component is folded inward in the transverse direction of the diaper, at which the side edges intersect the folding guides. Such a unique arrangement is effective to avoid the anxiety that these elastic members might move to the inside of the leg-holes in the vicinities of the crossing points during use of the diaper and thereby deteriorate the sealing effect desired around the wearer's legs. In this way, the apprehension of body fluids' leakage can be reliably eliminated.

What is claimed is:

1. A pull-on disposable diaper having a height direction, a transverse direction being orthogonal to said height direction and a back-and-forth direction, said diaper being substantially symmetric about a longitudinal center line extending in said height direction and bisecting a dimension of said diaper in said transverse direction, said diaper having an inner surface facing a wearer's body, an outer surface facing wearer's clothes, said diaper being composed of a front waist covering region destined to cover a wearer's front waist region, a rear waist covering region destined to cover a wearer's rear waist region and a crotch covering region destined to cover a wearer's crotch region so as to define a pants-like configuration having a waist-hole and a pair of leg-holes, and provided on said inner surface with a body fluid absorbing component extending over said crotch covering region and further extending into said front and rear waist covering regions, said pull-on disposable diaper further comprising:

said body fluid absorbing component comprising a liquid-absorbent core and a liquid-pervious cover sheet at least partially covering said core, having an inner surface facing said wearer's body, an outer surface facing away from said wearer's body and transversely opposite side edges extending parallel to each other beyond said crotch covering region into said front and rear waist covering regions and connecting said inner and outer surfaces to each other, said body fluid absorbing component being formed in said crotch covering region with a first folding guide extending from a transversely middle point between transversely opposite side edges to respective said side edges in said front waist covering region so as to describe a substantially V-shape, a second folding guide extending from a transversely middle point between transversely opposite side edges to respective said side edges to respective said side edges in said rear waist covering region so as to describe a substantially V-shape and a third folding guide extending in said transverse direction between said first and second folding guides, and said absorbing component being folded at least transversely opposite side edges on both sides of said longitudinal center line along said third folding guide so that said outer surfaces thereof face to each other and along said first and second folding guides so that said inner surfaces thereof face to each other; and elastic members provided in one of said front waist covering region, said rear waist covering region and said crotch covering region so as to intersect said side edges in vicinities of said leg-holes, one of said elastic members provided in said front waist covering region intersecting said side edges above first crossing points at which said side edges of said absorbing component intersect said first folding guide and one of said elastic members provided in said rear waist covering region intersecting said side edges above second crossing points at which said side edges of said absorbing component intersect said second folding guide;

wherein said absorbing component is folded along said first, second and third folding guides and tucked inwardly of said diaper to define inwardly portions;

opposing surfaces of said inwardly tucked portions are free of direct attachment to each other, allowing said absorbing component to be unfolded along all said first, second article third folding guides;

the opposing surfaces of said inwardly tucked portions are parts of the outer surface of said absorbing component; and said inwardly tucked portions are free of all elastic members which are directly bonded to at least one of said front waist covering region and said rear waist covering region.

* * * * *